United States Patent
Shinji et al.

(10) Patent No.: US 10,617,286 B2
(45) Date of Patent: Apr. 14, 2020

(54) ENDOSCOPE ILLUMINATION DEVICE AND ENDOSCOPE

(71) Applicant: OLYMPUS CORPORATION, Hachioji-shi, Tokyo (JP)

(72) Inventors: Sho Shinji, Tokyo (JP); Koichiro Furuta, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 407 days.

(21) Appl. No.: 15/494,164

(22) Filed: Apr. 21, 2017

(65) Prior Publication Data

US 2017/0215714 A1 Aug. 3, 2017

Related U.S. Application Data

(63) Continuation of application No. PCT/JP2014/083457, filed on Dec. 17, 2014.

(51) Int. Cl.
*A61B 1/06* (2006.01)
*A61B 1/00* (2006.01)
(Continued)

(52) U.S. Cl.
CPC ........ *A61B 1/0615* (2013.01); *A61B 1/00096* (2013.01); *A61B 1/00177* (2013.01);
(Continued)

(58) Field of Classification Search
CPC combination set(s) only.
See application file for complete search history.

(56) References Cited

U.S. PATENT DOCUMENTS 5,184,602 A * 2/1993 Anapliotis ......... A61B 1/00135
600/131
6,724,543 B1 * 4/2004 Chinniah ................ F21V 5/008
359/718
(Continued)

FOREIGN PATENT DOCUMENTS

CN 102209926 A 10/2011
CN 102687059 A 9/2012
(Continued)

OTHER PUBLICATIONS

International Search Report (ISR) and Written Opinion dated Mar. 31, 2015 issued in International Application No. PCT/JP2014/083457.

*Primary Examiner* — Anh Tuan T Nguyen
*Assistant Examiner* — Shankar Raj Ghimire
(74) *Attorney, Agent, or Firm* — Holtz, Holtz & Volek PC

(57) ABSTRACT

An endoscope illumination device includes: an illumination optical system including an entrance surface disposed along a circumferential direction centered on a predetermined axis and provided at one-end side in the direction of the predetermined axis, an emission surface positioned at an outermost side in a radial direction with respect to the predetermined axis and radially emitting illumination light entering from the entrance surface, a diffusion surface disposed at an intermediate position of an optical path of the illumination light between the entrance surface and the emission surface and transmitting and diffusing the illumination light; and a light emitting portion disposed closer to the one-end side than the entrance surface is and emitting, toward the entrance surface, the illumination light substantially in the direction of the axis.

14 Claims, 9 Drawing Sheets

(51) Int. Cl.
*A61B 1/04* (2006.01)
*G02B 23/24* (2006.01)
*H04N 5/225* (2006.01)
*G02B 3/08* (2006.01)

(52) U.S. Cl.
CPC ...... *A61B 1/00179* (2013.01); *A61B 1/00181* (2013.01); *A61B 1/04* (2013.01); *A61B 1/0607* (2013.01); *A61B 1/0623* (2013.01); *A61B 1/0684* (2013.01); *G02B 23/2461* (2013.01); *H04N 5/2256* (2013.01); *G02B 3/08* (2013.01); *G02B 23/2469* (2013.01); *H04N 2005/2255* (2013.01)

(56) References Cited

U.S. PATENT DOCUMENTS

| | | | | |
|---|---|---|---|---|
| 7,553,037 | B2* | 6/2009 | Sullivan | G01D 11/28 362/23.15 |
| 8,068,288 | B1* | 11/2011 | Pitou | G02B 3/08 359/743 |
| 9,261,254 | B2* | 2/2016 | de Lamberterie | F21S 41/141 |
| 9,854,960 | B2* | 1/2018 | Furuta | A61B 1/00163 |
| 10,098,528 | B2* | 10/2018 | Furuta | A61B 1/00096 |
| 2008/0242935 | A1 | 10/2008 | Inoue | |
| 2010/0312057 | A1* | 12/2010 | Konno | A61B 1/00177 600/162 |
| 2011/0211267 | A1 | 9/2011 | Takato | |
| 2011/0282148 | A1* | 11/2011 | Kase | A61B 1/00177 600/113 |
| 2012/0134159 | A1* | 5/2012 | Kamo | G02B 23/2461 362/308 |
| 2014/0346332 | A1* | 11/2014 | Honda | G02B 23/26 250/227.21 |
| 2014/0347878 | A1* | 11/2014 | Honda | G02B 23/2461 362/574 |
| 2016/0103312 | A1* | 4/2016 | Furuta | A61B 1/00096 362/558 |

FOREIGN PATENT DOCUMENTS

| | | |
|---|---|---|
| EP | 2815691 A1 | 12/2014 |
| JP | 2008237790 A | 10/2008 |
| JP | 2011048086 A | 3/2011 |
| JP | 2011228204 A | 11/2011 |
| JP | 5489689 B2 | 5/2014 |
| JP | 2014155526 A | 8/2014 |
| WO | 2014073426 A1 | 5/2014 |

* cited by examiner

ENDOSCOPE ILLUMINATION DEVICE AND ENDOSCOPE

CROSS-REFERENCE TO RELATED APPLICATIONS

This is a continuation of International Application PCT/JP2014/083457 which is hereby incorporated by reference herein in its entirety.

TECHNICAL FIELD

The present invention relates to an endoscope illumination device and an endoscope.

BACKGROUND ART

In an illumination device for lateral illumination, which is provided at a distal-end portion of an endoscope, a substantially semi-cylindrical light guiding member including a curved emission surface disposed at an outer peripheral surface of an insertion portion, a diffusion surface disposed so as to face the emission surface and having a light diffusion effect, and a proximal-end surface to which illumination light is supplied from a light guide has been conventionally used (for example, refer to PTL 1). The illumination light entering the proximal-end surface of the light guiding member from the light guide is reflected, by the diffusion surface, outwardly of the insertion portion in a radial direction. At this time, the illumination light is diffused by the diffusion surface, whereby brightness unevenness and color unevenness included in the illumination light emitted from the light guide are made uniform.

CITATION LIST

Patent Literature

{PTL 1} Publication of Japanese Patent No. 5489689

SUMMARY OF INVENTION

A first aspect of the present invention provides an endoscope illumination device including: an illumination optical system having an entrance surface disposed along a circumferential direction centered on a predetermined axis and provided at one-end side in the direction of the predetermined axis, and an emission surface positioned at an outermost side in a radial direction with respect to the predetermined axis and radially emitting illumination light entering from the entrance surface; and a light emitting portion disposed closer to the one-end side than the entrance surface is and emitting the illumination light substantially in the direction of the predetermined axis toward the entrance surface, wherein the illumination optical system further includes a diffusion surface disposed at an intermediate position on an optical path of the illumination light between the entrance surface and the emission surface and transmitting and diffusing the illumination light.

DESCRIPTION OF EMBODIMENTS

An endoscope illumination device 4 according to an embodiment of the present invention and an endoscope 1 including the same will be described below with reference to the drawings.

Figure 1:
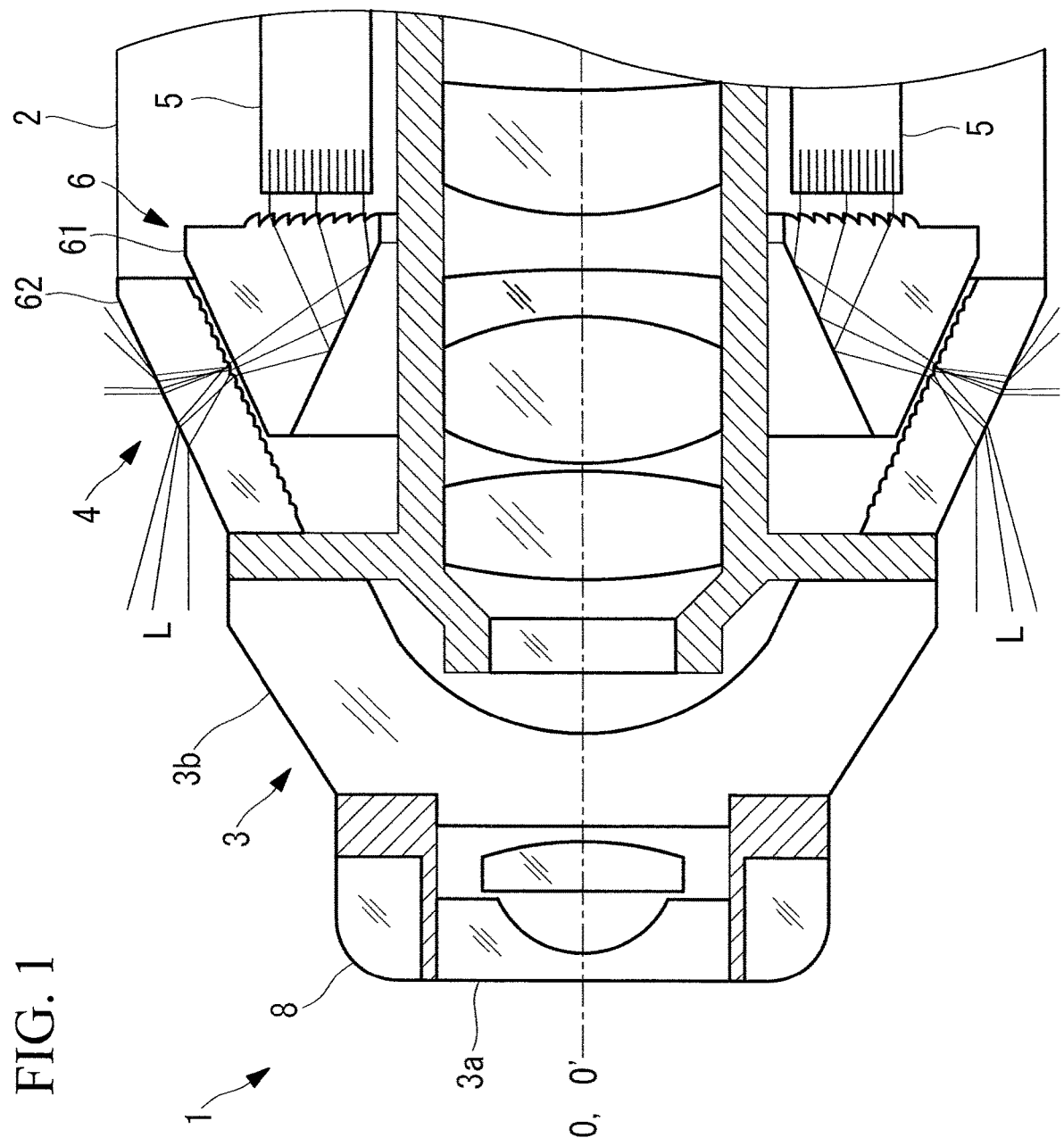
FIG. 1 is a cross-sectional view illustrating the configuration of a distal-end portion of an endoscope according to an embodiment of the present invention.

As shown in FIG. 1, the endoscope 1 according to this embodiment includes an elongated insertion portion 2 that can be inserted into the body, and an imaging optical system 3 and the endoscope illumination device 4 provided at a distal-end portion of the insertion portion 2.

The imaging optical system 3 includes a direct-viewing observation window 3a positioned at a distal-end surface of the insertion portion 2 and receiving light from a forward side of an optical axis O' thereof, and a side-viewing observation window 3b positioned at an outer peripheral surface of the insertion portion 2 and receiving light from a lateral side of the optical axis O' thereof. This allows the imaging optical system 3 to observe both forward and lateral sides with respect to the optical axis O'. Reference sign 8 indicates a direct-viewing illumination device for predominantly illuminating the forward side and around the forward side of the optical axis O'.

Figure 2A:
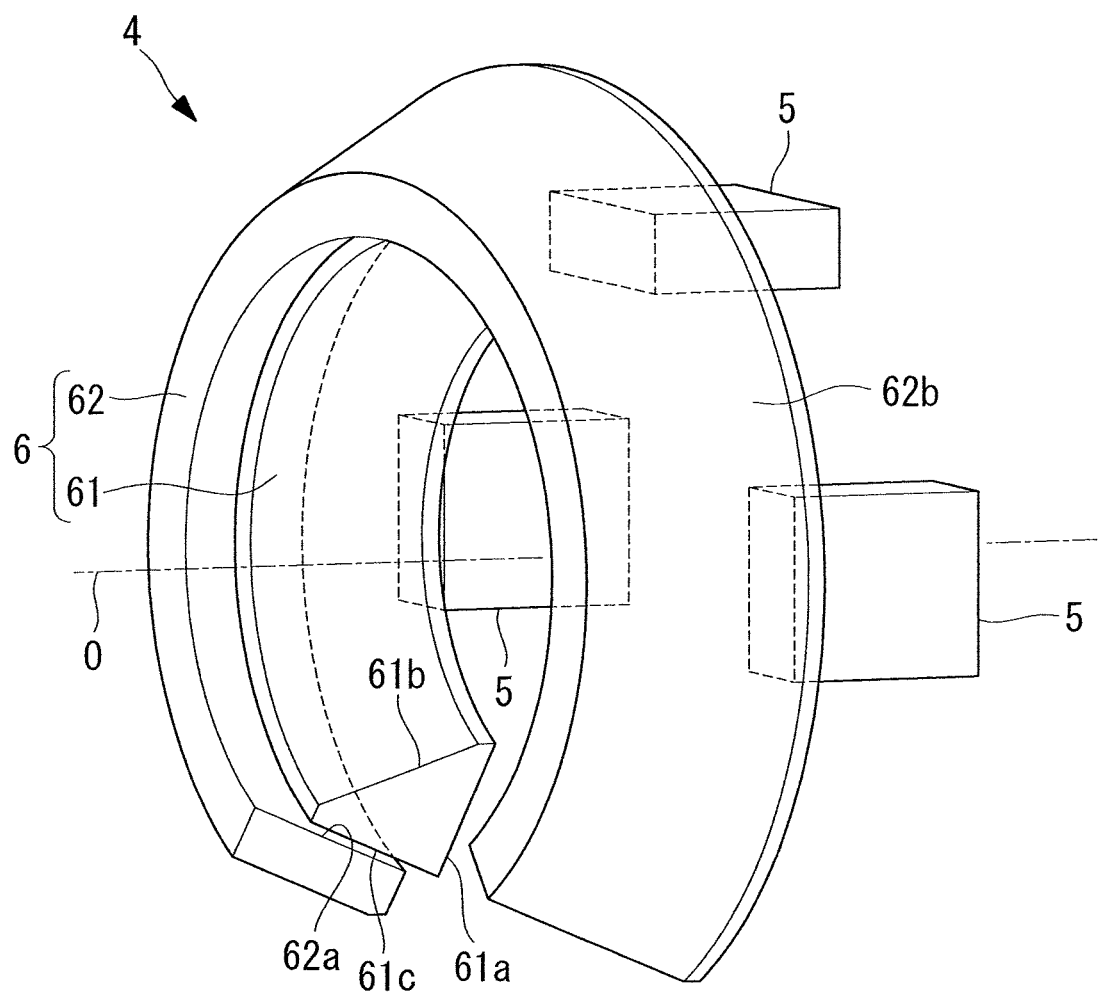
FIG. 2A is a perspective view of an endoscope illumination device in the endoscope in FIG. 1.
Figure 2B:
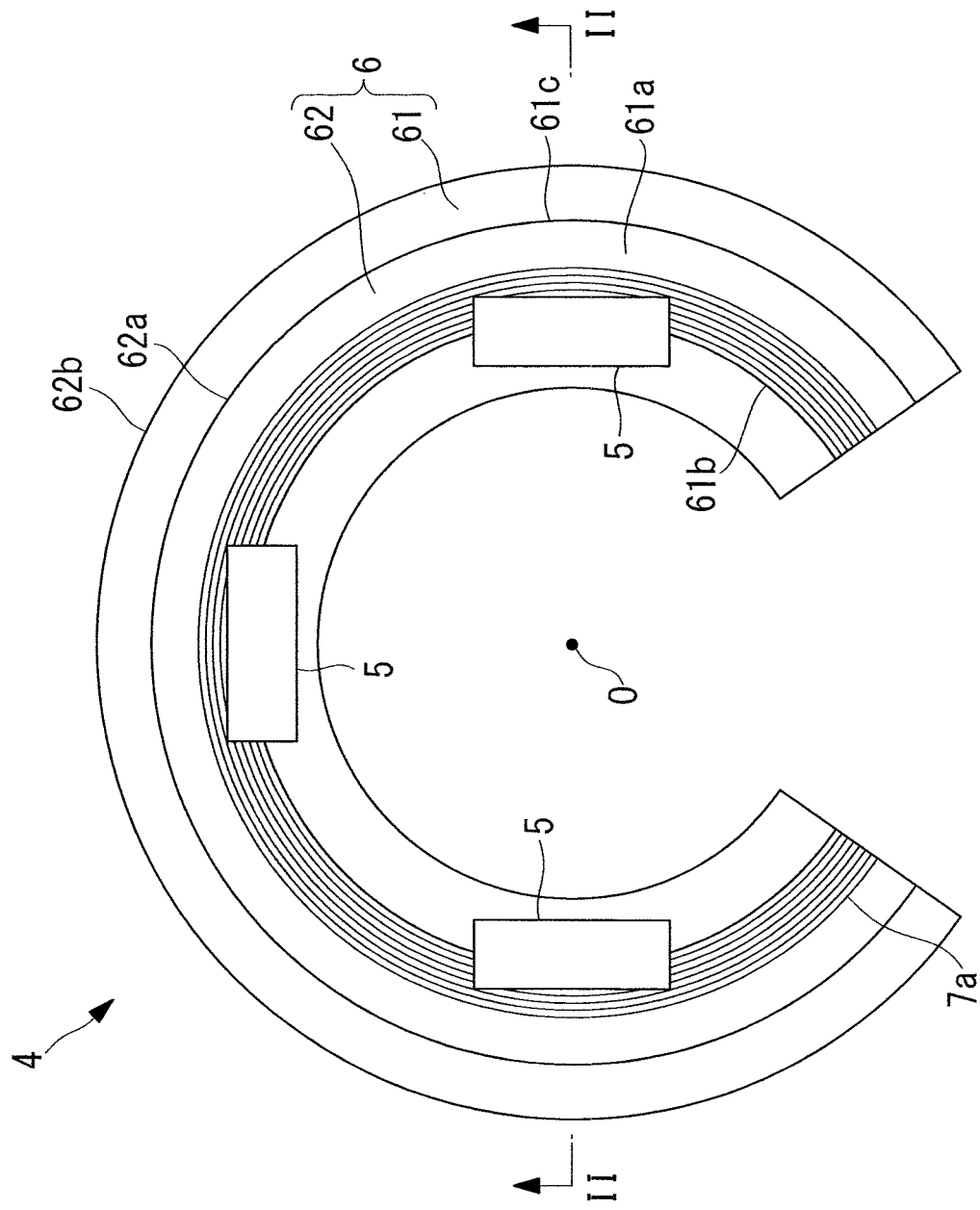
FIG. 2B is a rear view in which the endoscope illumination device in FIG. 2A is viewed from a proximal-end side.
Figure 2C:
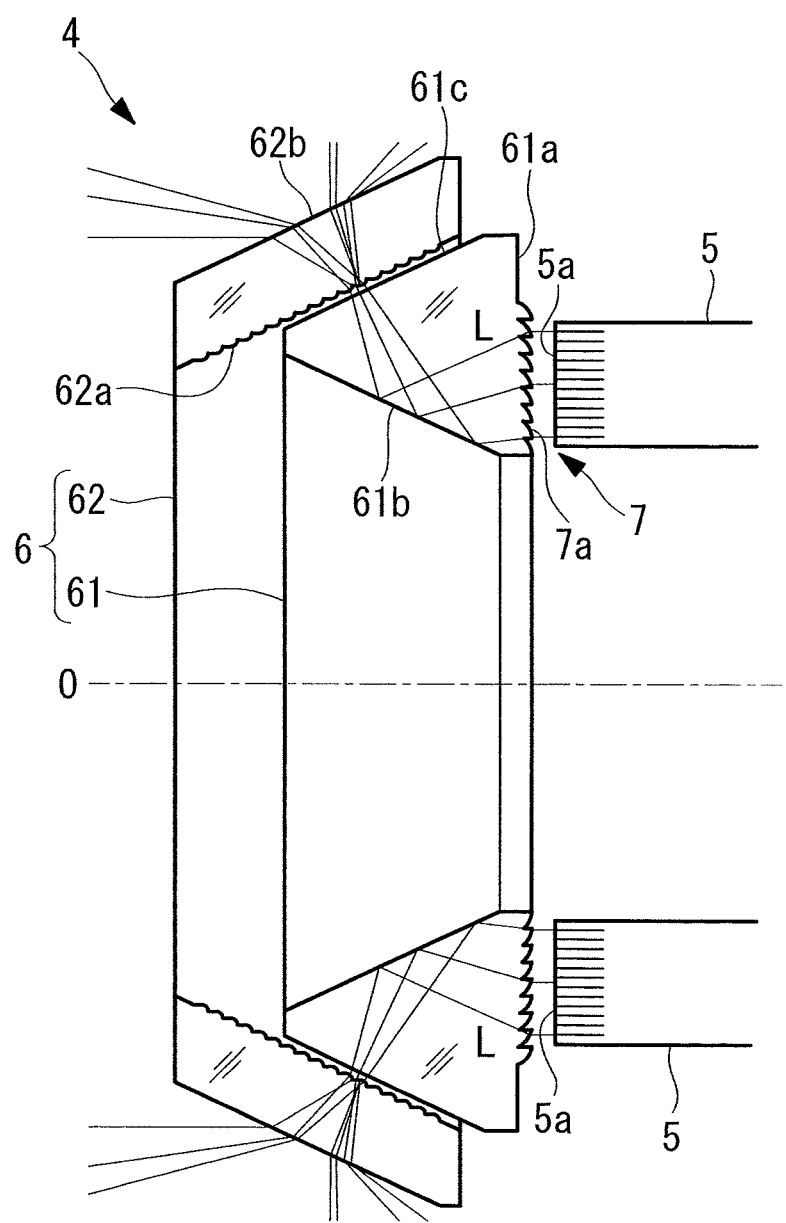
FIG. 2C is a cross-sectional view of the endoscope illumination device in FIG. 2B taken along line II-II.

The endoscope illumination device 4 is used for side-viewing in which a lateral side of the insertion portion 2 is illuminated, and is provided around the imaging optical system at a proximal-end side of the side-viewing observation window 3b. As shown in FIGS. 2A, 2B, and 2C, the endoscope illumination device 4 includes a plurality of light guides (light emitting portions) 5 disposed inside of the insertion portion 2 along the longitudinal direction, and an illumination optical system 6 provided at distal-end sides of the plurality of light guides 5 and radially emitting illumination light L supplied from the light guides 5 from the side surface of the insertion portion 2.

The light guides 5 are arranged so as to be spaced substantially equally from each other in a circumferential direction centered on a central axis O (described later) of the illumination optical system 6. Although three light guides 5 are shown in FIGS. 2A to 2C, the number of the light guides 5 can be changed arbitrarily. The light guides 5 have emission end surfaces 5a orthogonal to the longitudinal axis at the distal-end portions thereof, and the emission end surfaces 5a are disposed so as to be orthogonal to the central axis O. Entrance end surfaces (not shown) at proximal ends of the light guides 5 are connected to a light source device (not shown), and illumination light L supplied from the light source device to the entrance end surfaces is optically guided to the emission end surfaces 5a and emitted from the emission end surfaces 5a in the axial direction.

Note that the specific configuration of the light emitting portion is not limited to the light guides 5 and can be changed, as appropriate. For example, an LED may be used as the light emitting portion, and a light-emitting surface of the LED may be disposed so as to face an entrance surface 61a (described later) of the illumination optical system 6.

As shown in FIGS. 2A to 2C, the illumination optical system 6 has a substantially truncated conical cylindrical shape as a whole and is provided around the imaging optical system 3 in such a way that the central axis O (hereinafter referred to simply as an "axis O") thereof is substantially aligned with the optical axis O' of the imaging optical system 3. As shown in FIGS. 2A and 2B, part of the illumination optical system 6 in the circumferential direction may be cut out. Other members to be built into the insertion portion 2, such as, for example, a channel for a treatment tool and a light guide for a direct-viewing illumination device, etc. are disposed in a space formed by the cut-out.

The illumination optical system 6 includes a first optical member 61 having a substantially truncated conical cylindrical shape and a second optical member 62 having a substantially truncated conical cylindrical shape, and has a two-layer structure in which the first optical member 61 and the second optical member 62 are laminated in the radial direction. The first optical member 61 and the second optical member 62 are formed of a transparent medium having a high transmittance with respect to the illumination light L.

The first optical member 61 positioned at an inner side in the radial direction includes an entrance surface 61a formed of a proximal-end surface orthogonal to the axis O, a reflection surface 61b formed of an inner peripheral surface of the truncated conical surface shape and a diameter that gradually increases from the proximal-end side toward the distal-end side, and a transmission surface 61c formed of an outer peripheral surface of the truncated conical surface shape and a diameter that gradually decreases from the proximal-end side toward the distal-end side. Thus, the first optical member 61 has a substantially wedge shape having, at a cross-section including the axis O, the entrance surface 61a positioned at the proximal-end side, the reflection surface 61b positioned at the inner side in the radial direction, and the transmission surface 61c positioned at the outer side in the radial direction.

The entrance surface 61a is disposed so as to face the emission end surfaces 5a of the light guides 5 and to be substantially parallel thereto, and the illumination light L enters the entrance surface 61a in a direction of the axis O from the emission end surfaces 5a. Among the light emitted from the emission end surfaces 5a, substantially parallel light emitted in a direction perpendicular to the emission end surfaces 5a and along the axis O has the highest light intensity. For that reason, the substantially parallel light will be described as the illumination light L. On a region of the entrance surface 61a through which the illumination light L passes, a Fresnel lens surface (refraction surface, convergence surface) 7 is formed. The Fresnel lens surface refracts, inwardly in the radial direction, the entire illumination light L entering in a direction of the axis O and, at the same time, converts the illumination light L into a converging light flux.

As shown in FIG. 2B, the Fresnel lens surface 7 has many grooves 7a arranged coaxially at a regular pitch. The depth of the grooves 7a gradually increases from the inner side in the radial direction toward the outer side in the radial direction, which causes the illumination light L passing through the Fresnel lens surface 7 to be converged. The Fresnel lens surface 7 converts the illumination light L into a converging light flux having a convergence angle with which light flux diameters of the illumination light L at a diffusion surface 62a (described later) and an emission surface 62b (described later) become smaller than the light flux diameter of the illumination light L at the entrance surface 61a.

The reflection surface 61b is inclined with respect to the axis O in an orientation with which the distance from the axis O gradually increases from the proximal-end side toward the distal-end side, and reflects the illumination light L entering from the entrance surface 61a outwardly in the radial direction toward the transmission surface 61c.

The transmission surface 61c is inclined with respect to the axis O in an orientation with which the distance from the axis O gradually decreases from the proximal-end side toward the distal-end side, and transmits the illumination light L reflected by the reflection surface 61b.

The second optical member 62 positioned at the outer side in the radial direction includes a diffusion surface 62a formed of an inner peripheral surface having a truncated conical surface shape and a diameter that gradually decreases from the proximal-end side toward the distal-end side, and an emission surface 62b formed of an outer peripheral surface substantially parallel to the diffusion surface 62a. Thus, the second optical member 62 has, at a cross-section including the axis O, a substantially parallelogram shape.

The diffusion surface 62a is inclined at substantially the same angle as the transmission surface 61c and is disposed so as to face the transmission surface 61c and to be substantially parallel thereto.

Figure 3:
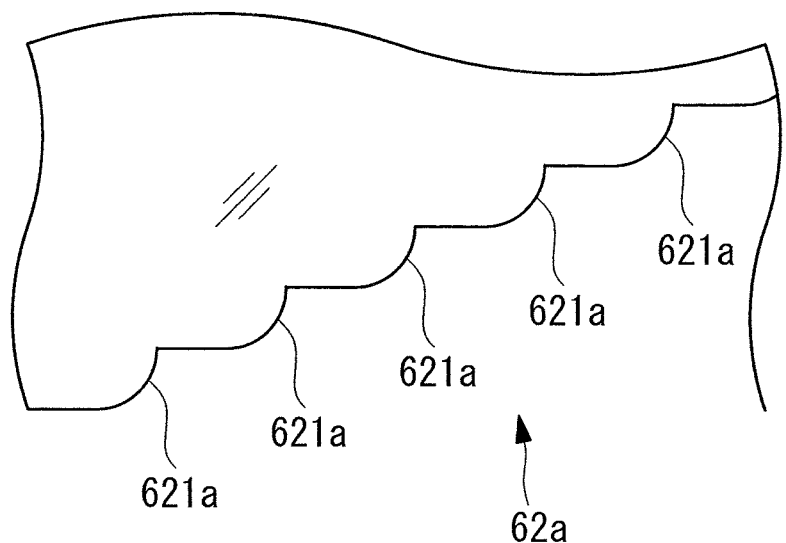
FIG. 3 is a partially enlarged view of the cross-sectional view in FIG. 2C illustrating an example of a lenticular lens formed on a diffusion surface of each of the endoscope illumination devices in FIGS. 2A to 2C.
Figure 4:
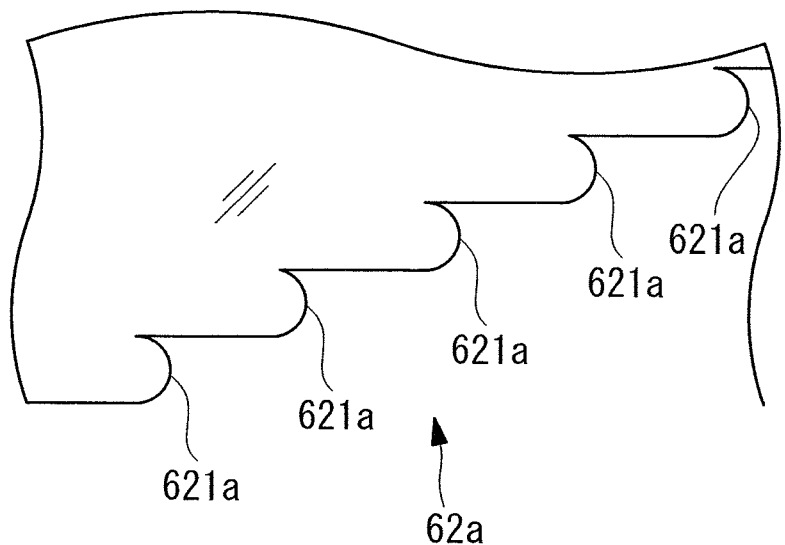
FIG. 4 is a partially enlarged view of the cross-sectional view in FIG. 2C illustrating another example of a lenticular lens formed on a diffusion surface of each of the endoscope illumination devices in FIGS. 2A to 2C.

A lenticular lens is formed on the diffusion surface 62a. FIGS. 3 and 4 show examples of the shape of the lenticular lens. As shown in FIGS. 3 and 4, the lenticular lens is formed by arranging, in the direction of the axis O (left/right direction in the figures), a plurality of convex lenses 621a having an elongated semi-cylindrical shape and extending in the shape of an arc centered on the axis O. The semi-cylindrical convex surfaces of the convex lenses 621a face the inner side in the radial direction and have a strong diverging action with respect to the illumination light L entering the convex surfaces. The diverging action causes the illumination light L transmitted through the lenticular lens to be diffused in various directions. In FIGS. 3 and 4, although the convex lenses 621a have the same curvature and are arranged with a regular pitch, the curvature and the pitch of the convex lenses 621a may be irregular.

For the diffusion surface 62a, any structure other than that of the lenticular lens may be adopted as long as it is a structure having a diffusion action with respect to the illumination light L transmitted through the diffusion surface 62a. For example, the diffusion surface 62a may be a roughened surface on which a fine indentation/projection structure like frosted glass is formed.

The emission surface 62b is formed of a smooth truncated conical surface substantially parallel to the diffusion surface 62a. The emission surface 62b emits, toward the lateral side and the forward side with respect to the axis O, the illumination light L transmitted through the diffusion surface 62a and diffused in various directions.

Figure 5:
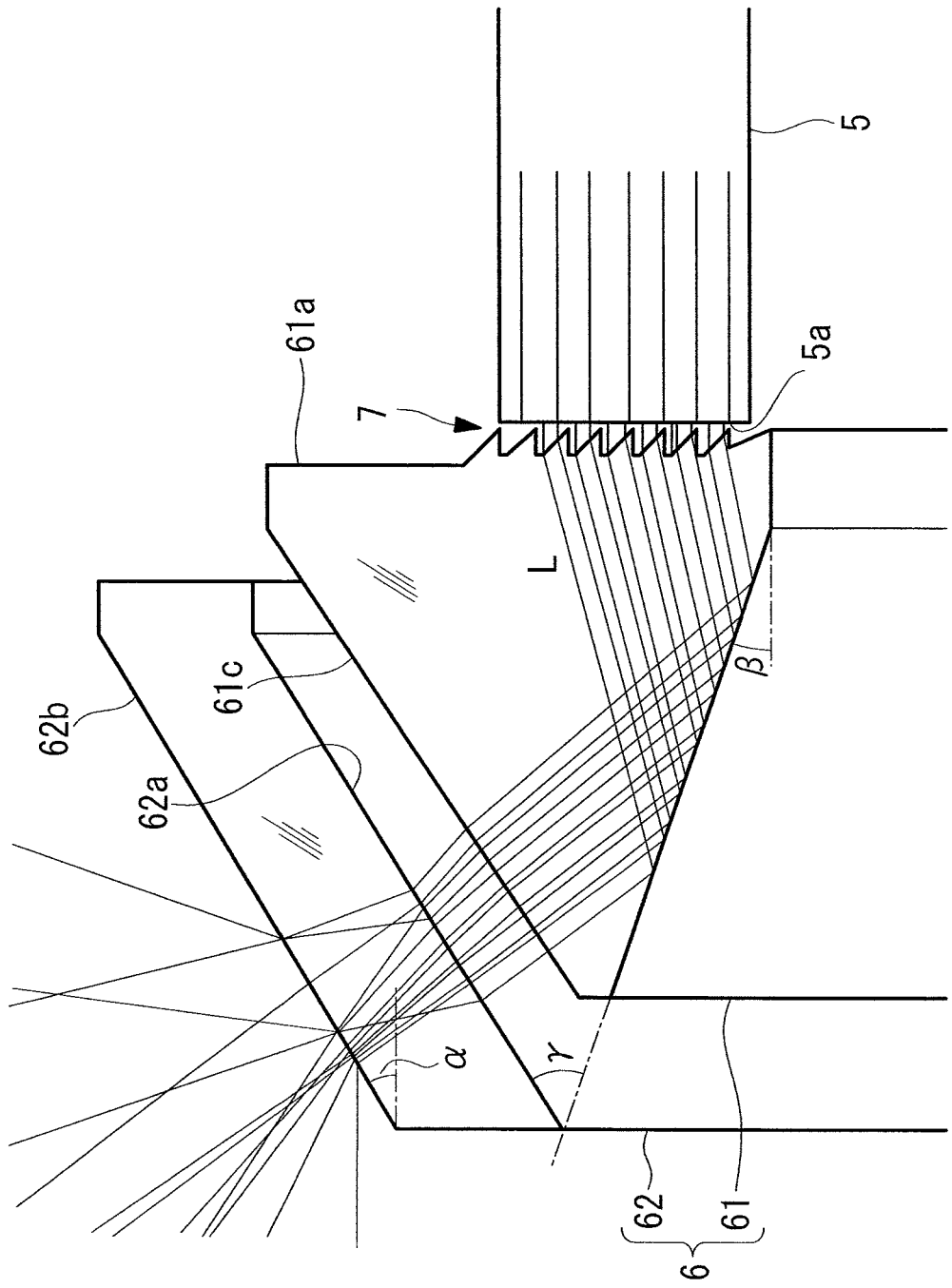
FIG. 5 is a partial cross-sectional view illustrating a modification of the endoscope illumination devices in FIGS. 2A to 2C.

Here, as shown in FIG. 5, it is preferable that an angle α formed by the emission surface 62b and the axis O, an angle β formed by the reflection surface 61b and the axis O, and an angle γ formed by the diffusion surface 62a and the reflection surface 61b satisfy the following conditional expressions. FIG. 5 shows, as an example, an illumination optical system 6 in which α=30°, β=20°, and γ=50°.

$$10° \leq \alpha \leq 40°$$

$$20° \leq \beta \leq 50°$$

$$40° \leq \gamma \leq 60°$$

By forming α within the above range, the illumination light L emitted from the emission surface 62b can be distributed evenly between the lateral side and the forward side, and the brightness of the illumination light L can be made uniform from the forward side to the lateral side. In the case where α is less than 10°, the amount of the illumination light L distributed to the forward side becomes smaller, making the forward side become darker, and in the case where α exceeds 40°, the amount of the illumination light L distributed to the lateral side becomes smaller, making the lateral side become darker.

By forming β within the above range, the entrance angle of the illumination light L to the diffusion surface 62a becomes approximately 90°, and the illumination light L is not reflected at the diffusion surface 62a but is transmitted through the diffusion surface 62a. This makes it possible to decrease the amount of the illumination light L lost at the diffusion surface 62a. In addition, the illumination light L emitted from the emission surface 62b can be distributed evenly between the lateral side and the forward side, and the brightness of the illumination light L can be made uniform from the forward side to the lateral side. In the case where β is less than 20° or exceeds 50°, some of the light beams of the illumination light L entering the diffusion surface 62a are not transmitted through the diffusion surface 62a but are totally reflected, and thus, a certain amount of the illumination light L is lost. In addition, compared with the amount of the illumination light L distributed to the forward side or the oblique rear side, the amount of the illumination light L distributed to the lateral side becomes smaller, and the lateral side becomes darker.

By forming γ within the above range, the entrance angle of the illumination light L to the diffusion surface 62a becomes approximately 90°, and the illumination light L is not reflected at the diffusion surface 62a but is transmitted through the diffusion surface 62a. This makes it possible to decrease the amount of the illumination light L lost at the diffusion surface 62a. In the case where γ is less than 40° or exceeds 60°, some of the light beams of the illumination light L entering the diffusion surface 62a are not transmitted through the diffusion surface 62a but are totally reflected, and thus, a certain amount of the illumination light L is lost.

Next, the operation of the thus-configured endoscope illumination device 4 and endoscope 1 will be described.

The illumination light L entering the entrance surface 61a of the first optical member 61 from the light source device in a direction of the axis O via the light guides 5 is converted into a converging light flux by the entrance surface 61a and, at the same time, is deflected inwardly in the radial direction so as to enter the reflection surface 61b. The illumination light L reflected on the reflection surface 61b outwardly in the radial direction is transmitted through the transmission surface 61c at a substantially right angle and is then diffused at the diffusion surface 62a. The illumination light L, after the light flux diameter thereof has been increased by the diffusion, is radially emitted toward the lateral side and the forward side of the insertion portion 2 from the emission surface 62b disposed on the outer peripheral surface of the insertion portion 2. This makes it possible to illuminate the lateral field of view and the forward field of view of the endoscope 1.

As described above, according to this embodiment, in the illumination optical system 6, the diffusion surface 62a is provided at an intermediate position on an optical path along which the illumination light L passes from the entrance surface 61a to the emission surface 62b. Therefore, the illumination light L is reliably diffused at least once by the diffusion surface 62a and is then emitted from the emission surface 62b. Thus, there is an advantage in that the light amount unevenness and color unevenness included in the illumination light L emitted from the light guides 5 can be reliably made uniform, and an object can be illuminated by using the illumination light L having uniform brightness and color.

In addition, there is an advantage in that the optical members 61, 62 can be made more compact by decreasing the light flux diameter of the illumination light L in the illumination optical system 6 with the Fresnel lens surface 7 formed on the entrance surface 61a. Furthermore, although it is possible to converge and deflect the illumination light L with a spherical lens surface, in the case where the Fresnel lens surface 7 is used, there is an advantage in that the entrance surface 61a can be made thinner in a direction of the axis O compared with the case where a spherical lens surface is used.

In addition, since the light flux diameter of the illumination light L increases after the light flux passes through the diffusion surface 62a, an optical surface positioned closer to the emission surface 62b than the diffusion surface 62a is on the optical path of the illumination light L needs to have a larger size in a direction of the axis O. Therefore, in order to make the illumination optical system 6 more compact, it is preferable that the diffusion surface 62a be provided closer to the emission surface 62b. However, the emission surface 62b needs to be smooth in order to prevent it from being soiled, and thus, it is not desirable to use the emission surface 62b as the diffusion surface 62a. According to this embodiment, by using the surface closest to the emission surface 62b as the diffusion surface 62a, there is an advantage in that the size of the emission surface 62b in the direction of the axis O can be minimized.

Figure 6:
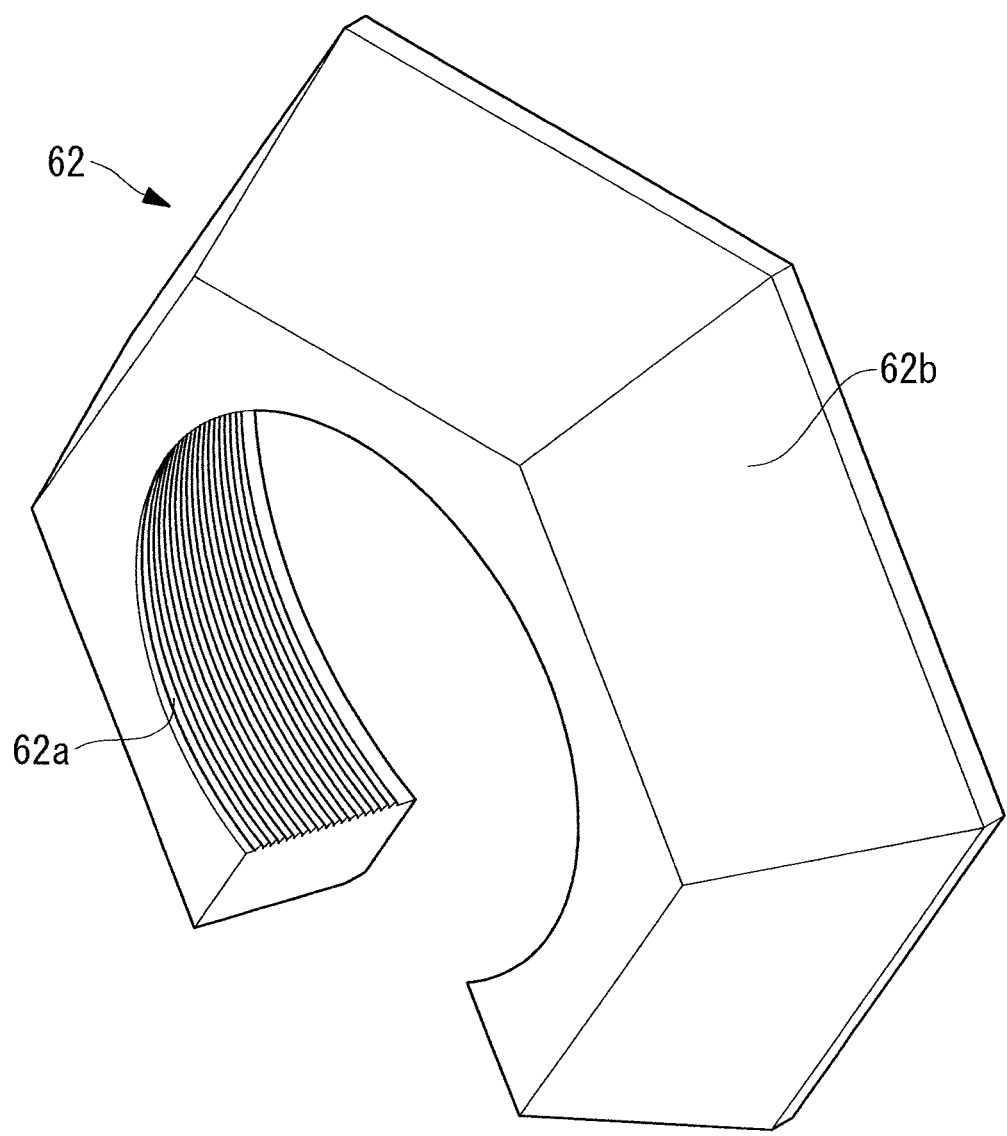
FIG. 6 is a perspective view illustrating another modification of the endoscope illumination devices in FIGS. 2A to 2C.

Note that, although the emission surface 62b is a truncated conical surface in this embodiment, alternatively, the emission surface 62b may be a polygonal truncated pyramid surface as shown in FIG. 6. Although the emission surface 62b having five planes is shown in FIG. 6, the number of the planes can be changed arbitrarily.

In the case where the emission surface 62b is a polygonal truncated pyramid surface, it is preferable that the same number of light guides 5 as the planes of the emission surface 62b be provided, and that each of the light guides 5 be disposed in correspondence with each plane. By doing so, the brightness of the illumination light L can be made uniform in a circumferential direction around the axis O.

Additionally, in this embodiment, although the entrance surface 61a has the Fresnel lens surface 7 that provides both a refraction action and a convergence action with respect to the illumination light L, the specific configuration of the entrance surface 61a is not limited to this configuration and can be changed, as appropriate, according to the required specifications for the endoscope illumination device 4.

Figure 7:
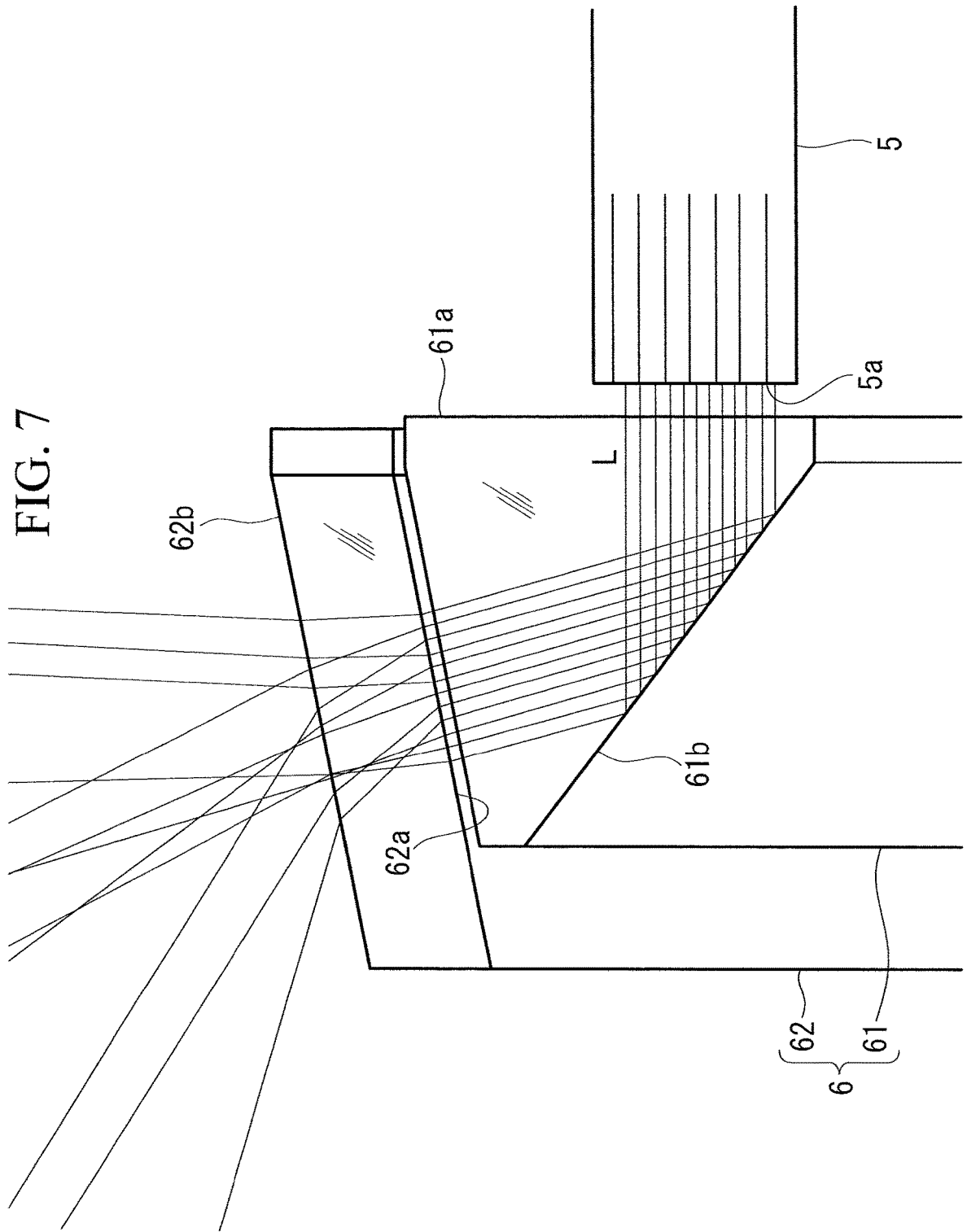
FIG. 7 is a partial cross-sectional view illustrating another modification of the endoscope illumination devices in FIGS. 2A to 2C.

For example, as shown in FIG. 7, the entrance surface 61a may be formed of a flat surface orthogonal to the axis O so as not to have a refraction action and a convergence action. In FIG. 7, α=15°, β=35°, and γ=50°. Alternatively, the entrance surface 61a may be formed of a spherical surface so as to have only a convergence action, or may be formed of a flat surface inclined with respect to the axis O so as to have only a refraction action.

Figure 8:
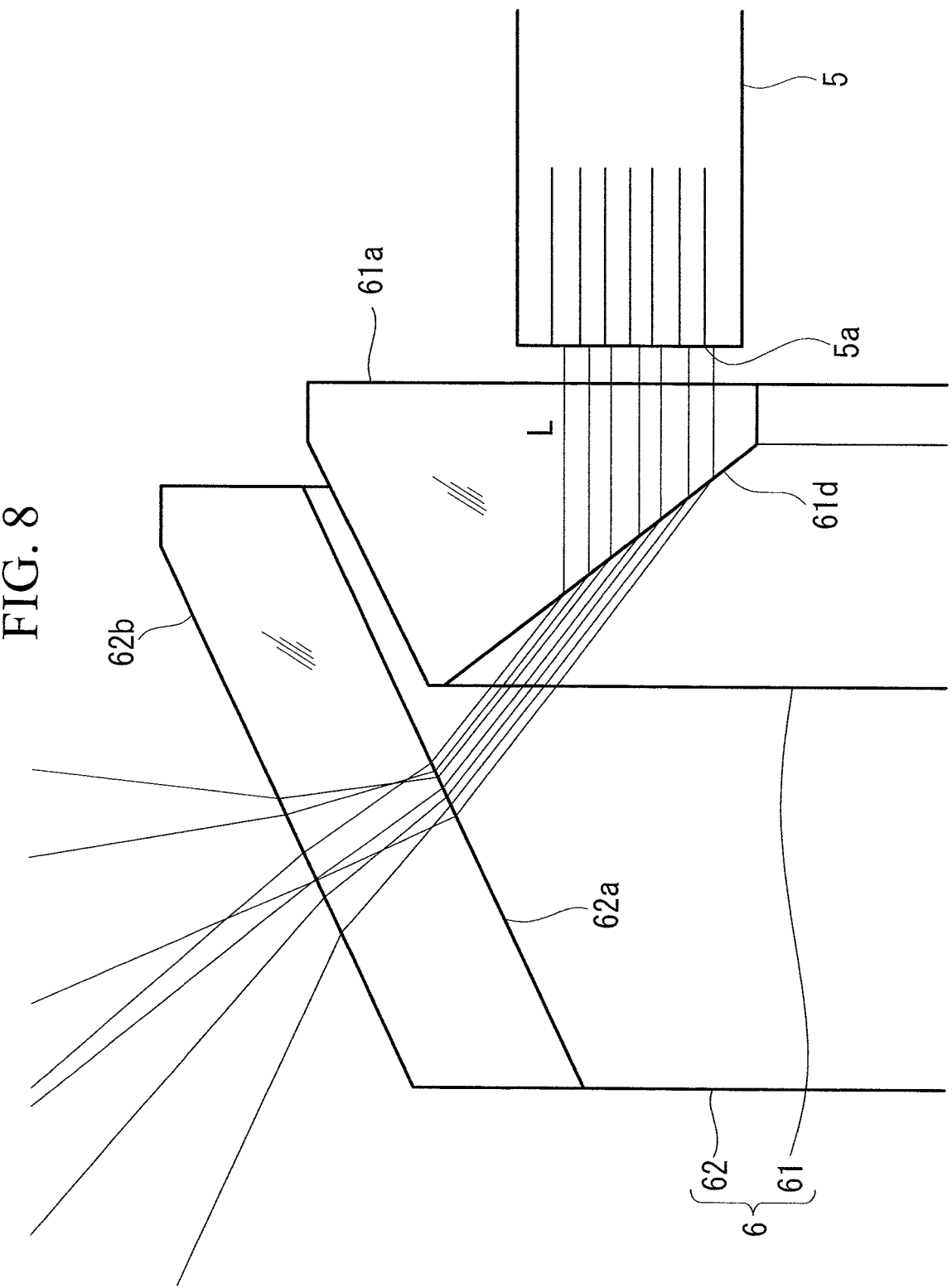
FIG. 8 is a partial cross-sectional view illustrating another modification of the endoscope illumination devices in FIGS. 2A to 2C.

In addition, in this embodiment, although the first optical member 61 has the reflection surface 61b reflecting the illumination light L entering from the entrance surface 61a in a direction of the axis O outwardly in the radial direction, alternatively, as shown in FIG. 8, the first optical member 61 may have a refraction surface 61d refracting the illumination light L entering from the entrance surface 61a in a direction of the axis O outwardly in the radial direction.

In addition, in this embodiment, although the inner peripheral surface of the second optical member 62 is the diffusion surface 62a, alternatively, another optical surface disposed at an intermediate position on an optical path of the illumination light L from the entrance surface 61a to the emission surface 62b and through which the illumination light L passes may be used as a diffusion surface. For example, the outer peripheral surface of the first optical member 61 may be used as a diffusion surface and the inner peripheral surface of the second optical member may be used as a transmission surface.

In addition, in this embodiment, although the illumination light L enters the illumination optical system 6 in a direction of the axis O from the light guides 5, alternatively, the illumination light L may enter in an oblique direction with respect to the axis O. For example, it is possible to omit the first optical member 61, use the diffusion surface 62a as an entrance surface, and cause the illumination light L to enter the diffusion surface 62a directly from the emission end surfaces 5a.

In addition, in this embodiment, although the illumination optical system 6 is formed of a single unit continuing in a circumferential direction, alternatively, the illumination optical system 6 may be divided into a plurality of units arranged in a circumferential direction centered on the axis O.

The above-described embodiment leads to the following invention.

A first aspect of the present invention provides an endoscope illumination device including: an illumination optical system having an entrance surface disposed along a circumferential direction centered on a predetermined axis and provided at one-end side in the direction of the predetermined axis, and an emission surface positioned at an outermost side in a radial direction with respect to the predetermined axis and radially emitting illumination light entering from the entrance surface; and a light emitting portion disposed closer to the one-end side than the entrance surface is and emitting the illumination light substantially in the direction of the predetermined axis toward the entrance surface, wherein the illumination optical system further includes a diffusion surface disposed at an intermediate position on an optical path of the illumination light between the entrance surface and the emission surface and transmitting and diffusing the illumination light.

According to the present invention, by radially emitting, from the emission surface, the illumination light entering the illumination optical system from the light emitting portion via the entrance surface, it is possible to illuminate an object positioned at a lateral side with respect to the predetermined axis.

In this case, in the illumination optical system, the illumination light is diffused reliably by transmitting, at least once, through the diffusion surface disposed at an intermediate position on an optical path between the entrance surface and the emission surface. This makes it possible to illuminate an object with uniform illumination light without brightness unevenness and color unevenness.

In the above-described first aspect, the emission surface of the illumination optical system may be inclined in an orientation with which a distance from the predetermined axis gradually decreases from the one-end side toward the other-end side.

By doing so, one-end side (forward side) of the predetermined axis and a lateral side can be illuminated at the same time with the illumination light emitted from the emission surface. In this case, by setting an inclination angle of the emission surface with respect to the predetermined axis to be 10° to 40°, inclusive, it becomes possible to distribute the illumination light between the lateral side and the forward side with a good balance.

In the above-described first aspect, the emission surface may have a truncated right conical shape centered on the predetermined axis.

By doing so, a good symmetry of the illumination light centered on the predetermined axis is achieved and the brightness of the illumination light can be made more uniform.

In the above-described first aspect, the diffusion surface may be disposed so as to face the emission surface in a radial direction, and the illumination optical system may have a reflection surface disposed on an optical path of the illumination light entering from the entrance surface and reflecting the illumination light outwardly in the radial direction toward the diffusion surface.

By doing so, the degree of freedom can be increased with respect to the designing of an entrance angle of the illumination light entering the entrance surface from the light emitting portion. In addition, this makes it possible to cause the optical path to be partially overlapped, which is advantageous for making the illumination optical system more compact.

In the above-described first aspect, the entrance surface may be a refraction surface deflecting, inwardly in the radial direction toward the reflection surface, the illumination light entering from the light emitting portion.

By doing so, an entrance angle of the illumination light on the diffusion surface can be made smaller (closer to 90°) and the amount of the illumination light lost at the diffusion surface can be reduced. In addition, it is possible to easily control an entrance angle of the illumination light on the reflection surface and the emission surface in accordance with a deflection angle of the illumination light by the refraction surface. In the case where the refraction surface is formed of a Fresnel lens surface, the refraction surface can be made thinner in the direction of the predetermined axis compared with the case where a spherical surface is used as the refraction surface.

In the above-described first aspect, on a plane including the predetermined axis, the entrance surface may be a convergence surface converting the illumination light emitted from the light emitting portion along and parallel to the predetermined axis into a converging light flux.

By doing so, a light flux diameter of the illumination light passing through the illumination optical system can be made smaller and the illumination optical system can be made more compact. In the case where the convergence surface is formed of a Fresnel lens surface, the convergence surface can be made thinner in the direction of the predetermined axis compared with the case where a spherical surface is used as the convergence surface.

In the above-described first aspect, on a plane including the predetermined axis, the convergence surface may convert the illumination light into a converging light flux having a convergence angle with which a light flux diameter of the illumination light at the diffusion surface becomes smaller than a light flux diameter of the illumination light at the convergence surface and the emission surface.

By doing so, the light flux diameter of the illumination light at the diffusion surface can be made smaller and the diffusion surface can be made smaller in the direction of the predetermined axis.

In the above-described first aspect, the reflection surface may be inclined in an orientation with which a distance from the predetermined axis gradually increases from the one-end side toward the other-end side, and an inclination angle of the reflection surface with respect to the predetermined axis may be 20° to 50°, inclusive.

By doing so, an entrance angle of the illumination light reflected by the reflection surface on the diffusion surface becomes smaller (closer to 90°) and the amount of the illumination light lost at the diffusion surface can be reduced. In addition, an emission angle of the illumination light from the emission surface with respect to the predetermined axis can be set within an appropriate range.

In the above-described first aspect, an angle formed by the diffusion surface and the reflection surface may be 40° to 60°, inclusive.

By doing so, an entrance angle of the illumination light reflected by the reflection surface on the diffusion surface becomes smaller (closer to 90°) and the amount of the illumination light lost at the diffusion surface can be reduced.

In the above-described first aspect, the illumination optical system may include: a first optical member having, on a cross-section including the predetermined axis, a substantially wedge shape formed of the entrance surface positioned at the one-end side, the reflection surface positioned at an inner side in the radial direction, and a transmission surface positioned at an outer side in the radial direction and transmitting the illumination light; and a second optical member disposed at an outer side of the first optical member in the radial direction and, on a cross-section including the predetermined axis, having the diffusion surface disposed so as to face the transmission surface, and the emission surface substantially parallel with the diffusion surface.

By doing so, a lateral side and a forward side can be illuminated with the illumination light entering the illumination optical system in a direction along the predetermined axis, and a size reduction in a radial direction with respect to the predetermined axis becomes possible.

In the above-described first aspect, the illumination optical system may include: a first optical member having, on a cross-section including the predetermined axis, a substantially wedge shape formed of the entrance surface positioned at the one-end side, the reflection surface positioned at an inner side in the radial direction, and the diffusion surface positioned at an outer side in the radial direction; and a second optical member disposed at an outer side of the first optical member in the radial direction and, on a cross-section including the predetermined axis, having a transmission surface disposed so as to face the diffusion surface and transmitting the illumination light, and the emission surface substantially parallel with the transmission surface.

A second aspect of the present invention provides an endoscope including an imaging optical system and any one of the above-described endoscope illumination devices disposed around the imaging optical system in such a way that the predetermined axis substantially matches an optical axis of the imaging optical system.

REFERENCE SIGNS LIST 1 endoscope
2 insertion portion
3 imaging optical system
4 endoscope illumination device
5 light guide (light emitting portion)
5a emission end surface
6 illumination optical system
61 first optical member
61a entrance surface
61b reflection surface
61c transmission surface
62 second optical member
62a diffusion surface
62b emission surface
7 Fresnel lens surface
O central axis
O' optical axis

The invention claimed is:
1. An endoscope illumination device comprising:
an illumination optical system having an axis and including:
an entrance surface disposed at least partially around the axis and centered on the axis, and
an emission surface positioned at an outermost side in a radial direction with respect to the axis and configured to radially emit illumination light that enters the illumination optical system through the entrance surface; and
a light emitting portion configured to emit the illumination light substantially in a direction of the axis toward the entrance surface,
wherein the illumination optical system further includes:
a diffusion surface disposed at an intermediate position on an optical path of the illumination light between the entrance surface and the emission surface, wherein the diffusion surface is configured to diffuse the illumination light, which is transmitted through the diffusion surface, and wherein the diffusion surface is disposed to face the emission surface in the radial direction, and
a reflection surface disposed on the optical path of the illumination light between the entrance surface and the emission surface, at a position between the entrance surface and the diffusion surface, the reflection surface being configured to reflect the illumination light outwardly in the radial direction toward the diffusion surface,
wherein the entrance surface is a refraction surface configured to deflect the illumination light inwardly in the radial direction toward the reflection surface, and
wherein the refraction surface is formed of a Fresnel lens surface.
2. The endoscope illumination device according to claim 1, wherein the emission surface of the illumination optical system is inclined such that a distance from the axis to the emission surface gradually decreases along the direction in which the light emitting portion emits the illumination light.

3. The endoscope illumination device according to claim 2, wherein an inclination angle of the emission surface with respect to the axis is 10° to 40°, inclusive.

4. The endoscope illumination device according to claim 1, wherein the emission surface has a truncated right conical shape centered on the axis.

5. The endoscope illumination device according to claim 1, wherein the reflection surface is inclined such that a distance from the axis to the reflection surface gradually increases along the direction in which the light emitting portion emits the illumination light, and
wherein an inclination angle of the reflection surface with respect to the axis is 20° to 50°, inclusive.

6. The endoscope illumination device according to claim 5, wherein an angle formed by the diffusion surface and the reflection surface is 40° to 60°, inclusive.

7. The endoscope illumination device according to claim 1, wherein the illumination optical system comprises:
a first optical member having, on a cross-section including the axis, a substantially wedge shape formed by the entrance surface, the reflection surface, and a transmission surface, wherein the entrance surface faces the light emitting portion, the reflection surface is positioned between the transmission surface and the axis in the radial direction, and the transmission surface is configured to transmit the illumination light; and
a second optical member having, on the cross-section including the axis, the diffusion surface disposed to face the transmission surface, and the emission surface substantially parallel with the diffusion surface,
wherein the first optical member is positioned between the second optical member and the axis, in the radial direction.

8. The endoscope illumination device according to claim 1, wherein the illumination optical system comprises:
a first optical member having, on a cross-section including the axis, a substantially wedge shape formed by the entrance surface, the reflection surface, and the diffusion surface, wherein the entrance surface faces the light emitting portion, and the reflection surface is positioned between the diffusion surface and the axis in the radial direction; and
a second optical member having, on the cross-section including the axis, a transmission surface disposed to face the diffusion surface and configured to transmit the illumination light, and the emission surface substantially parallel with the transmission surface,
wherein the first optical member is positioned between the second optical member and the axis, in the radial direction.

9. An endoscope comprising:
an imaging optical system; and
the endoscope illumination device according to claim 1 disposed around the imaging optical system in such a way that the axis of the illumination optical system substantially matches an optical axis of the imaging optical system.

10. An endoscope illumination device comprising:
an illumination optical system having an axis and including:
an entrance surface disposed at least partially around the axis and centered on the axis, and
an emission surface positioned at an outermost side in a radial direction with respect to the axis and configured to radially emit illumination light that enters the illumination optical system through the entrance surface; and
a light emitting portion configured to emit the illumination light substantially in a direction of the axis toward the entrance surface,
wherein the illumination optical system further includes a diffusion surface disposed at an intermediate position on an optical path of the illumination light between the entrance surface and the emission surface, wherein the diffusion surface is configured to diffuse the illumination light, which is transmitted through the diffusion surface, and
wherein, on a plane including the axis, the entrance surface is a convergence surface configured to convert the illumination light emitted from the light emitting portion along and parallel to the axis into a converging light flux.

11. The endoscope illumination device according to claim 10, wherein the convergence surface is formed of a Fresnel lens surface.

12. The endoscope illumination device according to claim 10, wherein, on the plane including the axis, the convergence surface converts the illumination light into the converging light flux such that the converging light flux has a convergence angle with which a light flux diameter of the illumination light at the diffusion surface becomes smaller than a light flux diameter of the illumination light at the convergence surface.

13. The endoscope illumination device according to claim 10, wherein, on the plane including the axis, the convergence surface converts the illumination light into the converging light flux such that the converging light flux has a convergence angle with which a light flux diameter of the illumination light at the diffusion surface becomes smaller than a light flux diameter of the illumination light at the emission surface.

14. An endoscope comprising:
an imaging optical system; and
the endoscope illumination device according to claim 10 disposed around the imaging optical system in such a way that the axis of the illumination optical system substantially matches an optical axis of the imaging optical system.

* * * * *